United States Patent
Endo et al.

(10) Patent No.: US 7,232,674 B2
(45) Date of Patent: Jun. 19, 2007

(54) PROCESS FOR PRODUCING α1,4-GALACTOSYLTRANSFERASE AND GALACTOSE-CONTAINING COMPLEX SUGAR

(75) Inventors: Tetsuo Endo, Palo Alto, CA (US); Satoshi Koizumi, Yokohama (JP)

(73) Assignee: Kyowa Hakko Kogyo Co., Ltd., Tokyo (JP)

( * ) Notice: Subject to any disclaimer, the term of this patent is extended or adjusted under 35 U.S.C. 154(b) by 236 days.

(21) Appl. No.: 10/490,879

(22) PCT Filed: Sep. 26, 2002

(86) PCT No.: PCT/JP02/09908

§ 371 (c)(1),
(2), (4) Date: Mar. 26, 2004

(87) PCT Pub. No.: WO03/029470

PCT Pub. Date: Apr. 10, 2003

(65) Prior Publication Data

US 2004/0253670 A1   Dec. 16, 2004

(30) Foreign Application Priority Data

Sep. 26, 2001   (JP) ............................. 2001-292797

(51) Int. Cl.
C12N 9/10 (2006.01)
C12N 1/19 (2006.01)
C12Q 1/68 (2006.01)
C12P 21/06 (2006.01)
C12P 13/04 (2006.01)
C07H 21/04 (2006.01)

(52) U.S. Cl. .................. 435/193; 435/6; 435/183; 435/320.1; 435/106; 435/252.33; 435/69.1; 536/23.2; 536/23.5; 536/23.6; 536/23.7

(58) Field of Classification Search ............... 435/193, 435/252.33, 106, 69.1; 536/23.2
See application file for complete search history.

(56) References Cited

FOREIGN PATENT DOCUMENTS

| CA | 2 315 885 | 8/2001 |
|---|---|---|
| WO | WO 95/00595 | 1/2000 |
| WO | WO 00/61724 | 4/2000 |

OTHER PUBLICATIONS

Koizumi, et al., "Large-scale production of UDP-galactose and globotriose by coupling metabolically engineered bacteria", *Nature Biotechnology*, vol. 16, No. 9 (1998), pp. 847-850.
Wakarchuk, et al., "Role of paired basic residues in the expression of active recombinant galactosytranferases from the . . . ", *Protein Engineering*, vol. 11, No. 4 (1998), pp. 295-302.
May, et al., Complete genomic sequence of *Pasteurella multocida*, Pm70, PNAS, vol. 98, No. 6 (2001), pp. 3460-3465.
Kojima, et al., "Molecular Cloning Globotriaosylceramide/CD77 Synthase, a . . . ", *The Journal of Biological Chemistry*, vol. 275, No. 20 (2000), pp. 15152-15156.
Keusch, et al., "Cloning of $Gb_3$ Synthase, the Key Enzyme in Globo-series . . . ", *The Journal of Biological Chemistry*, vol. 275, No. 33 (2000), pp. 25315-25321.
Steffensen, et al., "Cloning and Expression of the Hist-blood Group $P^k$ UDP-galactose:Galβ-4Glbcβ1-Cer . . . ", *The Journal of Biological Chemistry*, vol. 276, No. 22 (2000), pp. 16723-16729.
Endo, et al., "Large-scale production of oligosaccharides using engineered bacteria", *Current Opinion in Structural Biology*, vol. 10, No. 5 (2000), pp. 536-541.
Johnson, "Synthesis of oligosaccharides by bacterial enzymes", *Glycoconjugate Journal*, vol. 16 (1999), pp. 141-145.

*Primary Examiner*—Manjunath N. Rao
*Assistant Examiner*—Iqbal Chowdhury
(74) *Attorney, Agent, or Firm*—Fitzpatrick, Cella, Harper & Scinto

(57) ABSTRACT

The present invention can provide a process for producing a protein having α1.4-galactosyltransferase activity using a transformant comprising a DNA encoding a protein having α1.4-galactosyltransferase activity derived from a microorganism belonging to the genus *Pasteurella* and a process for producing a galactose-containing complex carbohydrate using a transformant capable of producing a protein having α1,4-galactosyltransferase activity derived from a microorganism.

6 Claims, 1 Drawing Sheet

SEQUENCE LISTING

<160> NUMBER OF SEQ ID NOS: 4

<210> SEQ ID NO 1
<211> LENGTH: 302
<212> TYPE: PRT
<213> ORGANISM: Pasteurella multocida

<400> SEQUENCE: 1

```
Met Asn Ile Leu Phe Val Ser Asp Asp Val Tyr Ala Arg His Leu Val
 1               5                  10                  15

Val Ala Ile Lys Ser Ile Ile Asn His Asn Glu Lys Gly Ile Ser Phe
             20                  25                  30

Tyr Ile Phe Asp Leu Gly Ile Lys Asp Glu Asn Lys Arg Asn Ile Asn
             35                  40                  45

Asp Ile Val Ser Ser Tyr Gly Ser Glu Val Asn Phe Ile Ala Val Asn
         50                  55                  60

Glu Lys Glu Phe Glu Ser Phe Pro Val Gln Ile Ser Tyr Ile Ser Leu
 65                  70                  75                  80

Ala Thr Tyr Ala Arg Leu Lys Ala Ala Glu Tyr Leu Pro Asp Asn Leu
                 85                  90                  95

Asn Lys Ile Ile Tyr Leu Asp Val Asp Val Leu Val Phe Asn Ser Leu
            100                 105                 110

Glu Met Leu Trp Asn Val Asp Val Asn Asn Phe Leu Thr Ala Ala Cys
            115                 120                 125

Tyr Asp Ser Phe Ile Glu Asn Glu Lys Ser Glu His Lys Lys Ser Ile
        130                 135                 140

Ser Met Ser Asp Lys Glu Tyr Tyr Phe Asn Ala Gly Val Met Leu Phe
145                 150                 155                 160

Asn Leu Asp Glu Trp Arg Lys Met Asp Val Phe Ser Arg Ala Leu Asp
                165                 170                 175

Leu Leu Ala Met Tyr Pro Asn Gln Met Ile Tyr Gln Asp Gln Asp Ile
            180                 185                 190

Leu Asn Ile Leu Phe Arg Asn Lys Val Cys Tyr Leu Asp Cys Arg Phe
        195                 200                 205

Asn Phe Met Pro Asn Gln Leu Glu Arg Ile Lys Gln Tyr His Lys Gly
    210                 215                 220

Lys Leu Ser Asn Leu His Ser Leu Glu Lys Thr Thr Met Pro Val Val
225                 230                 235                 240

Ile Ser His Tyr Cys Gly Pro Glu Lys Ala Trp His Ala Asp Cys Lys
                245                 250                 255

His Phe Asn Val Tyr Phe Tyr Gln Lys Ile Leu Ala Glu Ile Thr Arg
            260                 265                 270

Gly Thr Asp Lys Glu Arg Val Leu Ser Ile Lys Thr Tyr Leu Lys Ala
        275                 280                 285

Leu Ile Arg Arg Ile Arg Tyr Lys Phe Lys Tyr Gln Val Tyr
    290                 295                 300
```

<210> SEQ ID NO 2
<211> LENGTH: 906
<212> TYPE: DNA
<213> ORGANISM: Pasteurella multocida

<400> SEQUENCE: 2

```
atg aat att tta ttt gtt tct gat gat gtt tat gct aga cat ctg gtg      48
Met Asn Ile Leu Phe Val Ser Asp Asp Val Tyr Ala Arg His Leu Val
```

```
                1               5               10              15
gtt gcg att aaa agc att ata aat cat aat gaa aaa ggt att tca ttt      96
Val Ala Ile Lys Ser Ile Ile Asn His Asn Glu Lys Gly Ile Ser Phe
                    20              25              30 tat att ttt gat ttg ggt ata aag gat gaa aat aag aga aat att aat     144
Tyr Ile Phe Asp Leu Gly Ile Lys Asp Glu Asn Lys Arg Asn Ile Asn
            35              40              45 gat att gtt tct tct tat gga agt gaa gtc aac ttt att gct gtg aat     192
Asp Ile Val Ser Ser Tyr Gly Ser Glu Val Asn Phe Ile Ala Val Asn
        50              55              60 gag aaa gaa ttt gag agt ttt cct gtt caa att agt tat att tct tta     240
Glu Lys Glu Phe Glu Ser Phe Pro Val Gln Ile Ser Tyr Ile Ser Leu
 65              70              75              80 gca aca tat gca agg cta aaa gcg gca gag tat ttg ccg gat aat tta     288
Ala Thr Tyr Ala Arg Leu Lys Ala Ala Glu Tyr Leu Pro Asp Asn Leu
                    85              90              95 aat aaa att att tat tta gat gtt gat gtt ttg gtt ttt aac tca tta     336
Asn Lys Ile Ile Tyr Leu Asp Val Asp Val Leu Val Phe Asn Ser Leu
            100             105             110 gaa atg tta tgg aat gtt gat gtt aat aat ttt ctt acc gcg gcc tgt     384
Glu Met Leu Trp Asn Val Asp Val Asn Asn Phe Leu Thr Ala Ala Cys
        115             120             125 tat gat tct ttc atc gaa aat gaa aag tct gag cat aaa aaa tcg att     432
Tyr Asp Ser Phe Ile Glu Asn Glu Lys Ser Glu His Lys Lys Ser Ile
130             135             140 tca atg tca gat aag gaa tat tat ttt aat gca gga gta atg cta ttt     480
Ser Met Ser Asp Lys Glu Tyr Tyr Phe Asn Ala Gly Val Met Leu Phe
145             150             155             160 aat tta gat gaa tgg cgg aag atg gat gta ttc tca aga gct tta gac     528
Asn Leu Asp Glu Trp Arg Lys Met Asp Val Phe Ser Arg Ala Leu Asp
            165             170             175 ctg tta gct atg tat cct aat caa atg att tat cag gat caa gat ata     576
Leu Leu Ala Met Tyr Pro Asn Gln Met Ile Tyr Gln Asp Gln Asp Ile
        180             185             190 ttg aat atc ctt ttt agg aat aaa gtc tgt tat tta gat tgc aga ttt     624
Leu Asn Ile Leu Phe Arg Asn Lys Val Cys Tyr Leu Asp Cys Arg Phe
    195             200             205 aat ttc atg cca aat caa ctt gaa aga ata aaa caa tac cat aaa gga     672
Asn Phe Met Pro Asn Gln Leu Glu Arg Ile Lys Gln Tyr His Lys Gly
210             215             220 aaa ttg agc aac tta cat tct tta gaa aaa aca acg atg cct gtc gtt     720
Lys Leu Ser Asn Leu His Ser Leu Glu Lys Thr Thr Met Pro Val Val
225             230             235             240 att tca cat tat tgt ggt cca gaa aaa gcg tgg cat gcg gat tgt aaa     768
Ile Ser His Tyr Cys Gly Pro Glu Lys Ala Trp His Ala Asp Cys Lys
            245             250             255 cat ttt aat gta tat ttc tat cag aaa ata tta gca gaa ata acg aga     816
His Phe Asn Val Tyr Phe Tyr Gln Lys Ile Leu Ala Glu Ile Thr Arg
        260             265             270 ggc acg gat aaa gaa cgc gta tta tct ata aaa act tat ctc aag gcc     864
Gly Thr Asp Lys Glu Arg Val Leu Ser Ile Lys Thr Tyr Leu Lys Ala
    275             280             285 ttg att aga agg att aga tat aaa ttc aaa tat caa gtc tat             906
Leu Ile Arg Arg Ile Arg Tyr Lys Phe Lys Tyr Gln Val Tyr
290             295             300
```

<210> SEQ ID NO 3
<211> LENGTH: 27
<212> TYPE: DNA
<213> ORGANISM: Artificial Sequence

```
<220> FEATURE:
<223> OTHER INFORMATION: Description of Artificial Sequence:Synthetic
      DNA

<400> SEQUENCE: 3
tgagaagctt tatgaatatt ttatttg                                          27

<210> SEQ ID NO 4
<211> LENGTH: 28
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 4
acaaggatcc aatagttaat agacttga                                         28
```

PROCESS FOR PRODUCING α1,4-GALACTOSYLTRANSFERASE AND GALACTOSE-CONTAINING COMPLEX SUGAR

TECHNICAL FIELD

The present invention relates to a process for producing a protein having α1,4-galactosyltransferase activity using a transformant comprising a DNA encoding a protein having α1,4-galactosyltransferase activity and a process for producing a galactose-containing complex carbohydrate using the transformant.

BACKGROUND ART

As α1,4-galactosyltransferase and its genes, genes derived from animals [*J. Biol. Chem.*, 275, 15152 (2000), *J. Biol. Chem.*, 275 16723 (2000), Biochem. Biophys. Res. Commun., 227, 909 (1996)] and the like have been obtained. However, there is no example in which the α1,4-galactosyltransferase derived from an animal was expressed in a microorganism, such as *Escherichia coli*, as a protein having activity.

On the other hand, in the case of microorganisms, there is a report in which a gene encoding the α1,4-galactosyltransferase was obtained from a microorganism belonging to the genus *Neisseria* and the α1,4-galactosyltransferase was expressed in *Escherichia coli* using the gene [*Protein Eng.*, 11, 295 (1998), *Nat. Biotechnol.*, 16, 847 (1998)]. However, there is no report in which the gene is obtained from a microorganism belonging to the genus *Pasteurella*.

Also, full nucleotide sequence of genomic DNA in *Pasteurella multocida* PM70 have been determined [*Proc. Natl. Acad. Sci. USA*, 98, 3460 (2001)], and it has been suggested that pm1139 gene is a gene encoding α1,4-galactosyltransferase by homology search and the like (http://www.cbc.umn.edu/ResearchProjects/Pm/pmhome.html). However, there is no report that the gene product has α1,4-galactosyltransferase activity.

Among galactose-containing complex carbohydrates, especially, globotriose (Galα1,4Galβ1,4Glc) is a sugar part of globotriacylceramide (Gb3: Galα1,4Galβ1,4Glc-Cer) which is widely distributed as a Pk-type complex carbohydrate, and is known as an acceptor complex carbohydrate of vero toxin of *Escherichia coli* 0-157 and as an acceptor of Shiga toxin produced by *Shigella* sp. or enteroinvasive *Escherichia coli* [*J. Biol. Chem.*, 262, 8834 (1987), *Infect. Immun.*, 58, 611(1990)]. Also, pharmaceuticals in which the sugar part is bound to a carrier and the like have been developed.

DISCLOSURE OF THE INVENTION

Objects of the present invention are to provide a process for producing a protein having α1,4-galactosyltransferase activity using a transformant comprising a DNA encoding a protein having α1,4-galactosyltransferase activity and a process for producing a galactose-containing complex carbohydrate using the transformant.

In order to solve the above problems, the present inventors have conducted intensive studies and found that pm1139 gene product having homology with a known α1,4-galactosyltransferase has actually α1,4-galactosyltransferase activity, and obtained the DNA, and thus the present invention has been completed.

Specifically, the present invention relates to the following (1) to (29):

(1) A process for producing a protein having α1,4-galactosyltransferase activity, which comprises: culturing a transformant capable of producing a protein having α1,4-galactosyltransferase activity derived from a microorganism belonging to the genus *Pasteurella* in a medium to produce and accumulate the protein having α1,4-galactosyltransferase galactosyltransferase activity in the culture, and recovering the protein from the culture.

(2) The process according to (1), wherein the microorganism belonging to the genus *Pasteurella* is *Pasteurella multocida*.

(3) The process according to (1), wherein the protein having α1,4-galactosyltransferase activity is a protein comprising the amino acid sequence represented by SEQ ID NO:1.

(4) The process according to (1), wherein the protein having α1,4-galactosyltransferase activity is a protein which consists of an amino acid sequence in which at least one amino acid is deleted, substituted or added in the amino acid sequence represented by SEQ ID NO:1, and has α1,4-galactosyltransferase activity.

(5) The process according to (1), wherein the protein having α1,4-galactosyltransferase activity is a protein which has an identity of at least 80% with the amino acid sequence represented by SEQ ID NO:1, and has α1,4-galactosyltransferase activity.

(6) The process according to (1), wherein the transformant is a transformant which comprises a recombinant DNA comprising a DNA encoding a protein having α1,4-galactosyltransferase activity.

(7) The process according to (6), wherein the transformant is obtained by using a microorganism as a host cell.

(8) The process according to (7), wherein the microorganism is *Escherichia coli*.

(9) The process according to (6), wherein the DNA encoding the protein having α1,4-galactosyltransferase activity is a DNA comprising the nucleotide sequence represented by SEQ ID NO:2.

(10) The process according to (6), wherein the DNA encoding the protein having α1,4-galactosyltransferase activity is a DNA which hybridizes with a DNA comprising the nucleotide sequence represented by SEQ ID NO:2 under stringent conditions, and encodes a protein having α1,4-galactosyltransferase activity.

(11) A process for producing a galactose-containing complex carbohydrate, which comprises: allowing a culture of a transformant capable of producing a protein having α1,4-galactosyltransferase activity or a treated product of the culture as an enzyme source, uridine-5'-diphosphogalactose and an acceptor complex carbohydrate to be present in an aqueous medium to produce and accumulate the galactose-containing complex carbohydrate in the aqueous medium, and recovering the galactose-containing complex carbohydrate from the aqueous medium.

(12) The process according to (11), wherein the treated product of the culture is selected from the group consisting of a concentrated product of the culture, a dried product of the culture, cells obtained by centrifuging the culture, a dried product of the cells, a freeze-dried product of the cells, a surfactant-treated product of the cells, an ultrasonic-treated product of the cells, a mechanically disrupted product of the cells, a solvent-treated product of the cells, an enzyme-treated product of the cells, a protein fraction of the cells, an immobilized product of the cells and an enzyme preparation obtained by extracting from the cells.

(13) The process according to (11), wherein the acceptor complex carbohydrate is a complex carbohydrate comprising an oligosaccharide having galactose in its non-reducing terminal.

(14) The process according to (13), wherein the oligosaccharide having galactose in the non-reducing terminal is an oligosaccharide selected from the group consisting of lactose, N-acetyllactosamine, lacto-N-tetraose, para-lacto-N-neohexaose and lacto-N-neotetraose.

(15) The process according to (11), wherein the acceptor complex carbohydrate is a complex carbohydrate selected from the group consisting of lactose, N-acetyllactosamine, lacto-N-tetraose, para-lacto-N-neohexaose and lacto-N-neotetraose.

(16) The process according to (11), wherein the protein having α1,4-galactosyltransferase is a protein derived from a microorganism belonging to the genus *Pasteurella*.

(17) The process according to (16), wherein the microorganism belonging to the genus *Pasteurella* is *Pasteurella multocida*.

(18) The process according to (11), wherein the protein having α1,4-galactosyltransferase activity is a protein comprising the amino acid sequence represented by SEQ ID NO:1.

(19) The process according to (11), wherein the protein having α1,4-galactosyltransferase activity is a protein which consists of an amino acid sequence in which at least one amino acid is deleted, substituted or added in the amino acid sequence represented by SEQ ID NO:1, and has α1,4-galactosyltransferase activity.

(20) The process according to (11), wherein the protein having α1,4-galactosyltransferase activity is a protein which has an identity of at least 80% with the amino acid sequence represented by SEQ ID NO:1, and has α1,4-galactosyltransferase activity.

(21) The process according to (11), wherein the transformant is a transformant which comprises a recombinant DNA comprising a DNA encoding a protein having α1,4-galactosyltransferase activity.

(22) The process according to (21), wherein the transformant is obtained by using a microorganism as a host cell.

(23) The process according to (22), wherein the microorganism is *Escherichia coli*.

(24) The process according to (21), wherein the DNA encoding the protein having α1,4-galactosyltransferase activity is a DNA comprising the nucleotide sequence represented by SEQ ID NO:2.

(25) The process according to (21), wherein the DNA encoding the protein having α1,4-galactosyltransferase activity is a DNA which hybridizes with a DNA comprising the nucleotide sequence represented by SEQ ID NO:2 under stringent conditions, and encodes a protein having α1,4-galactosyltransferase activity.

(26) A protein having α1,4-galactosyltransferase activity, which comprises the amino acid sequence represented by SEQ ID NO:1.

(27) A protein which consists of an amino acid sequence in which at least one amino acid is deleted, substituted or added in the amino acid sequence represented by SEQ ID NO:1, and has α1,4-galactosyltransferase activity.

(28) A protein which has an identity of at least 80% with the amino acid sequence represented by SEQ ID NO:1, and has α1,4-galactosyltransferase activity.

(29) A DNA which hybridizes with the DNA comprising the nucleotide sequence represented by SEQ ID NO:2 under stringent condition and encodes a protein having α1,4-galactosyltransferase activity.

The present invention is explained below in detail.

The protein having α1,4-galactosyltransferase activity of the present invention includes the protein having α1,4-galactosyltransferase activity derived from a microorganisms belonging to the genus *Pasteurella*, preferably the protein having α1,4-galactosyltransferase activity derived from *Pasteurella multocida*.

The protein having α1,4-galactosyltransferase activity used in the process for producing a galactose-containing complex carbohydrate of the present invention is not particularly limited, so long as it is a protein having α1,4-galactosyltransferase activity. It is preferably a protein having α1,4-galactosyltransferase activity derived from a microorganism belonging to the genus *Pasteurella*, and more preferably a protein having α1,4-galactosyltransferase activity derived from *Pasteurella multocida*.

Specifically, the protein includes a protein comprising the amino acid sequence represented by SEQ ID NO:1; a protein which consists of an amino acid sequence in which at least one amino acid is deleted, substituted or added in the amino acid sequence represented by SEQ ID NO:1, and has α1,4-galactosyltransferase activity; and a protein which has an identity of at least 80% with the amino acid sequence represented by SEQ ID NO:1, and has α1,4-galactosyltransferase activity.

The protein which consists of an amino acid sequence in which at least one amino acid is deleted, substituted or added, and has α1,4-galactosyltransferase activity can be obtained, for example, by introducing mutation(s) to a DNA encoding a protein comprising the amino acid sequence represented by SEQ ID NO:1 according to a method for introducing site-directed mutagenesis described in *Molecular Cloning, A Laboratory Manual*, Second Edition, Cold Spring Harbor Laboratory Press (1989) (hereinafter referred to as "*Molecular Cloning*, Second Edition"); *Current Protocols in Molecular Biology*, John Wiley & Sons (1987-1997) (hereinafter referred to as "*Current Protocols in Molecular Biology*"); *Nucleic Acids. Research*, 10, 6487 (1982); *Proc. Natl. Acad. Sci. USA*, 79, 6409 (1982); *Gene*, 34 315 (1985); *Nucleic Acids. Research*, 13 4431 (1985); *Proc. Natl. Acad. Sci. USA*, 82, 488 (1985) and the like.

The number of the amino acids which are deleted, substituted or added is not particularly limited; however, it is such a number that deletion, substitution or addition can be carried out by a known method such as method for introducing site-directed mutagenesis. The number is 1 to several tens, preferably 1 to 20, more preferably 1 to 10, and most preferably 1 to 5.

The deletion, substitution or addition of at least one amino acid residue in the amino acid sequence represented by SEQ ID NO:1 means that one or at least two amino acids are deleted, substituted or added at any position in the same sequence. The deletion, substitution or addition can be carried out in the same amino acid sequence simultaneously. Also, the amino acid residue substituted or added can be natural or non-natural. The natural amino acid residue includes L-alanine, L-asparagine, L-aspartic acid, L-glutamine, L-glutamic acid, glycine, L-histidine, L-isoleucine, L-leucine, L-lysine, L-arginine, L-methionine, L-phenylalanine, L-proline, L-serine, L-threonine, L-tryptophan, L-tyrosine, L-valine, L-cysteine, and the like.

Herein, examples of amino acid residues which are substituted with each other are shown below. Amino acid residues in the same group can readily be substituted with each other.

Group A:
leucine, isoleucine, norleucine, valine, norvaline, alanine, 2-aminobutanoic acid, methionine, O-methylserine, t-butylglycine, t-butylalanine, cyclohexylalanine;

Group B:
aspartic acid, glutamic acid, isoasparatic acid, isoglutamic acid, 2-aminoadipic acid, 2-aminosuberic acid;

Group C:
asparagine, glutamine;

Group D:
lysine, arginine, ornithine, 2,4-diaminobutanoic acid, 2,3-diaminopropionic acid;

Group E:
proline, 3-hydroxyproline, 4-hydroxyproline;

Group F:
serine, threonine, homoserine;

Group G:
phenylalanine, tyrosine.

Also, in order that the protein which consists of an amino acid sequence in which at least one amino acid is deleted, substituted or added has α1,4-galactosyltransferase activity, the protein has an identity of preferably at least 60% or more, more preferably 80% or more, and most preferably 95% or more, with the amino acid sequence represented by SEQ ID NO:1.

The identity of an amino acid sequence or a nucleotide sequence can be determined by using the algorithm BLAST by Karlin and Altschul [*Proc. Natl. Acad. Sci. USA*, 90,5873 (1993)] or FASTA [*Methods Enzymol.*, 183, 63 (1990)]. The programs called BLASTN and BLASTX have developed based on the above algorithm BLAST [*J. Mol. Biol*, 215, 403 (1990)]. In the case of analyzing a nucleotide sequence by BLASTN based on BLAST, for example, the parameter can be set to score=100, wordlength=12. Also, in the case of analyzing an amino acid sequence by BLASTX based on BLAST, for example, the parameter can be set to score=50, wordlength=3. When BLAST and Gapped BLAST programs are used, a default parameter of each program can be used. The specific analysis methods of using the above programs are known (http://www.ncbi.nlm.nih.gov.).

The transformant used in the production of the protein having α1,4-galactosyltransferase activity of the present invention includes a transformant comprising a DNA encoding a protein having α1,4-galactosyltransferase. The DNA encoding the protein having α1,4-galactosyltransferase includes (1) a DNA encoding a protein comprising the amino acid sequence represented by SEQ ID NO:1;
(2) a DNA comprising the nucleotide sequence represented by SEQ ID NO:2;
(3) a DNA encoding a protein which consists of an amino acid sequence in which at least one amino acid is deleted, substituted or added in the amino acid sequence represented by SEQ ID NO:1, and has α1,4-galactosyltransferase activity;
(4) a DNA encoding a protein which has an identity of at least 80% with the amino acid sequence represented by SEQ ID NO:1, and has α1,4-galactosyltransferase activity; and
(5) a DNA which hybridizes with a DNA comprising the nucleotide sequence represented by SEQ ID NO:2 under stringent conditions, and encodes a protein having α1,4-galactosyltransferase activity.

The DNA which is hybridizable under stringent conditions is a DNA obtained by colony hybridization, plaque hybridization, Southern hybridization or the like using, as a probe, a part or a full length of a DNA comprising the nucleotide sequence represented by SEQ ID NO:2. Specifically, the DNA includes a DNA which can be identified by carrying out hybridization at 65° C. in the presence of 0.7–1.0 mol/l NaCl using a filter on which a DNA prepared from colonies or plaques is immobilized, and then washing the filter with 0.1× to 2×SSC solution (the composition of 1×SSC solution contains 150 mmol/l sodium chloride and 15 mmol/l sodium citrate) at 65° C. The hybridization can be carried out in accordance with a known method described in, for example, *Molecular Cloning*, Second Edition; *Current Protocols in Molecular Biology*; *DNA Cloning* 1: *Core Techniques, A Practical Approach*, Second Edition, Oxford University (1995) or the like. Specifically, the DNA which is hybridizable includes a DNA having an identity of at least 60% or more, preferably 80% or more, and more preferably 95% or more, with the nucleotide sequence represented by SEQ ID NO:2 when calculated based on the above parameters using above BLAST, FASTA or the like.

[1] Preparation of a DNA Used in the Process for Producing the Present Invention (1) Selection of a DNA Encoding the Protein Having α1,4-galactosyltransferase Activity Using Database The full nucleotide sequence of the genomic DNA in *Pasteurella multocida* PM70 was determined [*Proc. Natl. Acad. Sci., USA*, 98 3460 (2001)], and the DNA encoding the protein having α1,4-galactosyltransferase activity can be selected by carrying out gene search, homology search and the like by using a known sialyltransferase gene based on the nucleotide sequence of the genomic DNA [http://www.cbc.umn.edu/ResearchProjects/Pm/pmhome.html, http://www.ncbi.nlm.nih.gov /BLAST/].

(2) Preparation of a DNA Used in the Production Process of the Present Invention The DNA encoding the protein having α1,4-galactosyltransferase activity used in the production process of the present invention can be prepared from a microorganism belonging to the genus *Pasteurella*. The microorganism belonging to the genus *Pasteurella* includes *Pasteurella multocida*, and specifically *Pasteurella multocida* PM70 (available from Minnesota University) and the like.

The microorganism belonging to *Pasteurella multocida* can be cultured by a known method [for example, *FEMS Microbiol. Lett.*, 166, 289 (1998)].

After the culturing, a chromosomal DNA of the microorganism can be isolated and purified by a known method (for example, method described in *Current Protocols in Molecular Biology*).

A DNA fragment containing the DNA used in the process for producing the present invention can be obtained by preparing a primer based on the nucleotide sequence of the genomic DNA selected in the item (1) and then carrying out PCR [*PCR Protocols*, Academic Press (1990)] using the genomic DNA as a template.

Furthermore, the DNA of interest can be obtained according to a hybridization method by using the synthetic DNA designed based on the nucleotide sequence of the genomic DNA as a probe.

The nucleotide sequence of the DNA can be determined by inserting the obtained DNA as it is or after digestion with an appropriate restriction enzyme, into a vector according to the usual method, and carrying out analysis by the generally used nucleotide sequence analysis method such as the dideoxy method [*Proc. Natl. Acad. Sci. USA*, 74 5463 (1977)] or a method comprising the use of an apparatus for nucleotide sequence analysis such as 373A.DNA Sequencer (manufactured by Perkin-Elmer).

Based on the nucleotide sequence thus determined, the DNA of interest can also be prepared by chemical synthesis using, for example, DNA Synthesizer 8905 manufactured by Perceptive Biosystems or the like.

The vector into which the DNA of the present invention is ligated includes pBluescript II KS(+) (manufactured by Stratagene), pDIRECT [*Nucleic Acids Res.*, 18, 6069 (1990)], pCR-Script Amp SK(+) (manufactured by Stratagene), pT7Blue manufactured by Novagen), pCR II (manufactured by Invitrogen), pCR-TRAP (manufactured by Genehunter) and the like.

A recombinant DNA pPM1139SK which comprises the DNA comprising the nucleotide sequence represented by SEQ ID NO:2 has been deposited on Sep. 13, 2001, as FERM BP-7732, in International Patent Organism Depositary, National Institute of Advanced Industrial Science and Technology (Central 6, 1-1, Higashi 1-Chome Tsukuba, Ibaraki, 305-8566, Japan).

The microorganism containing the recombinant DNA which comprises the DNA comprising the sequence represented by SEQ ID NO:2 includes *Escherichia coli* and the like.

*Escherichia coli* includes *Escherichia coli* XL1-Blue, Escherichia coli XL2-Blue, *Escherichia coli* DH1, *Escherichia coli* MC1000, *Escherichia coli* KY3276, *Escherichia coli* W1485, *Escherichia coli* JM109, *Escherichia coli* HB101, *Escherichia coli* No.49, *Escherichia coli* W3110, *Escherichia coli* NY49, *Escherichia coli* MP347, *Escherichia coli* NM522, *Escherichia coli* ME8415 and the like.

Any method can be used in the introduction method of the recombinant DNA, so long as it is a method for introducing DNA into the host cell. Examples include the method using a calcium ion [*Proc. Natl. Acad. Sci. USA*, 69, 2110 (1972)], the protoplast method (Japanese Published Unexamined Patent Application No. 248394/88), electroporation [*Nucleic Acid Res.*, 16, 6127 (1988)] and the like.

*Escherichia coli* containing the recombinant DNA which comprises the DNA comprising the nucleotide sequence represented by SEQ ID NO:2 includes *Escherichia coli* NM522/pPM1139.

[2] Preparation of the Protein of the Present Invention

The protein having α1,4-galactosyltransferase activity can be produced by expressing the DNA obtained by the method of the above item [1] in a host cell, for example, as shown below, by using a method described in *Molecular Cloning, Second Edition, Current Protocols in Molecular Biology* or the like.

Based on the above DNA, a DNA fragment of an appropriate length containing a portion which encodes the protein can be prepared, if necessary. In addition, productivity of the protein can be improved by substituting a nucleotide in the nucleotide sequence of the protein-coding region so that it has the most suitable codons for the expression in the host.

A recombinant DNA is prepared by inserting the DNA into a downstream of the promoter of an appropriate expression vector.

A transformant capable of producing the protein used for the process of the present invention can be obtained by introducing the recombinant DNA into a host cell suitable for the expression vector.

Any bacteria, yeasts, animal cells, insect cells, plant cells and the like can be used as the host cell, so long as it can express the gene of interest.

The expression vectors include those which can replicate autonomously in the above host cell or those which can be integrated into a chromosome and have a promoter at such a position that the DNA used in the production process of the present invention can be transcribed.

When a procaryote such as bacterium is used as the host cell, it is preferred that the recombinant DNA which comprises the DNA encoding the protein of the present invention can replicate autonomously in the procaryote, and that the recombinant vector contains a promoter, a ribosome binding sequence, the DNA of the present invention and a transcription termination sequence. The vector may further comprise a gene regulating the promoter.

The expression vector includes pHelix1 (manufactured by Roche Diagnostics), pKK233-2 (manufactured by Amersham Pharmacia Biotech), pSE280 (manufactured by Invitrogen), pGEMEX-1 (manufactured by Promega), pQE-8 (manufactured by QIAGEN), pET-3 (manufactured by Novagen), pKYP10 (Japanese Published Unexamined Patent Application No. 110600/83), pKYP200 [*Agric. Biol. Chem.*, 48, 669 (1984)], pLSA1 [*Agric. Biol. Chem.*, 53, 277 (1989)], pGEL1 [*Proc. Natl. Acad. Sci. USA*, 82, 4306 (1985)], pBluescript II SK(+), pBluescript II KS(−) (manufactured by Stratagene), pTrS30 [prepared from *Escherichia coli* JM109/pTrS30 (FERM BP-5407)], pTrS32 [prepared from *Escherichia coli* JM109/pTrS32 (FERM BP-5408)], pPAC31 (WO98/12343), pUC19 [*Gene*, 33, 103 (1985)], pSTV28 (manufactured by Takara Shuzo), pUC118 (manufactured by Takara Shuzo), pPA1 (Japanese Published Unexamined Patent Application No. 233798/88) and the like.

Any promoter can be used, so long as it can function in the host cell. Examples include promoters derived from *Escherichia coli*, phage and the like, such as trp promoter ($P_{trp}$), lac promoter ($P_{lac}$), $P_L$ promoter, $P_R$ promoter and $P_{SE}$ promoter, SPO1 promoter, SPO2 promoter, penP promoter and the like. Also, artificially designed and modified promoters, such as a promoter in which two $P_{trp}$ are linked in tandem, tac promoter, lacT7 promoter and letI promoter, can be used.

It is preferred to use a plasmid in which the space between Shine-Dalgarno sequence, which is the ribosome binding sequence, and the initiation codon is adjusted to an appropriate distance (for example, 6 to 18 nucleotides).

The transcription termination sequence to express the DNA used in the production process of the present invention is not essential for the recombinant DNA. However, it is preferred to lie a transcription terminating sequence immediately downstream of the structural gene.

The procaryotes include microorganisms belonging to the genera *Escherichia, Serratia, Bacillus, Brevibacterium, Corynebacterium, Microbacterium, Pseudomonas* and the like. Examples include *Escherichia coli* XL1-Blue, *Escherichia coli* XL2-Blue, *Escherichia coli* DH1, *Escherichia coli* NM522, *Escherichia coli* MC1000, *Escherichia coli* KY3276, *Escherichia coli* W1485, *Escherichia coli* JM109, *Escherichia coli* HB101, *Escherichia coli* No. 49, *Escherichia coli* W3110, *Escherichia coli* NY49, *Serratia ficaria, Serratia fonticola, Serratia liquefaciens, Serratia marcescens, Bacillus subtilis, Bacillus amyloliquefaciens, Brevibacterium immariophilum* ATCC 14068, *Brevibacterium saccharolyticum* ATCC 14066, *Corynebacterium ammoniagenes, Corynebacterium glutamicum* ATCC 13032, *Corynebacterium glutamicum* ATCC 14067, *Corynebacterium glutamicum* ATCC 13869, *Corynebacterium acetoaci-*

*dophilum* ATCC 13870, *Microbacterium ammoniaphilum* ATCC 15354, *Pseudomonas* sp. D-0110 and the like.

Introduction of the recombinant DNA can be carried out by any methods for introducing DNA into the above-described host cells, such as the method using a calcium ion [*Proc. Natl. Acad. Sci. USA*, 69 2110 (1972)], the protoplast method (Japanese Published Unexamined Patent Application No. 248394/88) and electroporation [*Nucleic Acids Res.*, 16 6127 (1988)].

When a yeast cell is used as the host cell, the expression vector includes YEp13 (ATCC 37115), YEp24 (ATCC 37051), YCp50(ATCC 37419), pHS19, pHS15 and the like.

Any promoter can be used so long as it can function in yeast. Examples include PHO5 promoter, PGK promoter, GAP promoter, ADH promoter, gal 1 promoter, gal 10 promoter, a heat shock polypeptide promoter, MFα1 promoter, CUP 1 promoter and the like.

The host cell includes yeast strain belonging to the genera *Saccharomyces, Schizosaccharomyces, Kluyveromyces, Trichosporon, Schwanniomyces, Pichia, Candida* and the like. Examples include *Saccharomyces cerevisiae, Schizosaccharomyces pombe, Kluyveromyces lactis, Trichosporon pullulans, Schwanniomyces alluvius, Pichia pastoris, Candida utilis* and the like.

Introduction of the recombinant DNA can be carried out by any of the methods for introducing DNA into yeast, such as electroporation [*Methods. Enzymol.*, 194, 182 (1990)], the spheroplast method [*Proc. Natl. Acad Sci. USA*, 81, 4889 (1984)] and the lithium acetate method [*J. Bacteriol.*, 153, 163 (1983)].

When an animal cell is used as the host, the expression vector includes pcDNAI (available from Funakoshi) and pcDM8 (available from Funakoshi), pAGE107 (Japanese Published Unexamined Patent Application No. 22979/91), pAS3-3 (Japanese Published Unexamined Patent Application No. 227075/90), pcDNAI/Amp (manufactured by Invitrogen), pREP4 (manufactured by Invitrogen), pAGE103 [*J. Biochem.*, 101 1307 (1987)], pAGE210, pAMo, pAMoA and the like.

Any promoter can be used, so long as it can function in an animal cell. Examples include a promoter of IE (immediate early) gene of cytomegalovirus (CMV), SV40 early promoter, a metallothionein promoter, a promoter of retrovirus, a heat shock promoter, SRα promoter and the like. Also, the enhancer of the IE gene of human CMV can be used together with the promoter.

The host cell includes mouse myeloma cell, rat myeloma cell, mouse hybridoma cell, human Namalwa cell, Namalwa KJM-1 cell, human fetal kidney cell, human leukemia cell, African grivet kidney cell, Chinese hamster ovary (CH(O) cell, HST5637 (Japanese Published Unexamined Patent Application No. 299/88) and the like.

The mouse myeloma cell includes SP2/0, NS0 and the like. The rat myeloma cell includes YB2/0 and the like. The human fetal kidney cell includes HEK293 (ATCC: CRL-1573) and the like. The human leukemia cell includes BALL-1 and the like. The African grivet kidney cell includes COS-1, COS-7 and the like.

Introduction of the recombinant DNA into animal cells can be carried out by any of methods for introducing DNA into animal cells, such as electroporation [*Cytotechnology*, 3, 133 (1990)], the calcium phosphate method (Japanese Published Unexamined Patent Application No. 227075/90), the lipofection method [*Proc. Natl. Acad. Sci. USA*, 84, 7413 (1987)], and the method described in *Virology*, 52, 456 (1973).

When an insect cell is used as the host, the protein can be produced by a known method described in, for example, *Baculovirus Expression Vectors, A Laboratory Manual*, W. H. Freeman and Company, New York (1992), *Molecular Biology, A Laboratory Manual, Current Protocols in Molecular Biology, Bio/Technology*, 6, 47 (1988) or the like.

Specifically, a recombinant gene transfer vector and baculovirus are co-transfected into an insect cell to obtain a recombinant virus in a supernatant of the culture of its insect cell, and then an insect cell is infected with the resulting recombinant virus to produce the protein.

The transfer vector used in the method includes pVL1392, pVL1393 and pBlueBacIII (all manufactured by Invitrogen), and the like.

The baculovirus includes *Autographa californica* nuclear polyhedrosis virus which infects insects of the family *Barathra* and the like.

The insect cell includes *Spodoptera frugiperda* ovary cell, *Trichoplusia ni* ovary cell, silkworm ovary-derived culturing cell and the like.

*Spodoptera frugiperda* ovary cell includes Sf9 and Sf21 (*Baculovirus Expression Vectors, A Laboratory Manual*) and the like. *Trichoplusia ni* ovary cell includes High 5 and BTI-TN-5B1-4 (manufactured by Invitrogen) and the like. The cell line derived from silkworm ovary cell includes *Bombyx mori* N4 and the like.

The method for co-transfecting the above transfer vector and the above baculovirus for the preparation of the recombinant virus includes the calcium phosphate method (Japanese Published Unexamined Patent Application No. 227075/90), the lipofection method [*Proc. Natl. Acad. Sci. USA*, 84, 7413 (1987)] and the like.

When a plant cell is used as the host cell, the expression vector includes Ti plasmid, a tobacco mosaic virus vector, and the like.

As the promoter, any promoter can be used, so long as it can function in a plant cell. Examples include 35S promoter of cauliflower mosaic virus (CaMV), rice actin 1 promoter and the like.

The host cell includes a plant cell and the like, such as tobacco, potato, tomato, carrot, soybean, rape, alfalfa, rice, wheat and barley.

Introduction of the recombinant vector is carried out by any of methods for introducing DNA into a plant cell, such as *Agrobacterium* method (Japanese Published Unexamined Patent Application No. 140885/84, Japanese Published Unexamined Patent Application No. 70080/85, WO 94/00977), electroporation (Japanese Published Unexamined Patent Application No. 251887/85) and the method using a particle gun (Japanese Patent Nos. 2606856 and 2517813).

The protein having α1,4-galactosyltransferase activity can be produced by culturing the transformant thus obtained in a medium to produce and accumulate the protein having α1,4-galactosyltransferase activity in the culture, and recovering it from the culture.

Culturing of the transformant used in the process production of the present invention in a medium is carried out according to the conventional method as used in culturing of the host.

As a medium for culturing the transformant obtained by using, as the host, prokaryote such as *Escherichia coli*, or eukaryote such as yeast, either a natural medium or a synthetic medium may be used, so long as it contains a carbon source, a nitrogen source, an inorganic salt and the like which can be assimilated by the organism and the transformant can be cultured efficiently.

Any carbon source can be used, so long as the organism can assimilate, and it includes carbohydrates, such as glucose, fructose, sucrose, molasses containing them, starch and starch hydrolysate; organic acids, such as acetic acid and propionic acid; alcohols, such as ethanol and propanol; and the like.

The nitrogen source includes ammonia, various ammonium salts of inorganic acids or organic acids, such as ammonium chloride, ammonium sulfate, ammonium acetate and ammonium phosphate; other nitrogen-containing compounds; peptone; meat extract; yeast extract; corn steep liquor; casein hydrolysate; soybean meal and soybean meal hydrolysate; various fermented cells and digested matter thereof; and the like.

The inorganic salt includes potassium dihydrogen phosphate, dipotassium hydrogen phosphate, magnesium phosphate, magnesium sulfate, sodium chloride, ferrous sulfate, manganese sulfate, copper sulfate, calcium carbonate and the like.

Culturing is usually carried out under aerobic conditions by shaking culture, submerged spinner culture under aeration or the like. The culturing temperature is preferably from 15 to 40° C., and the culturing time is generally from 5 hours to 7 days. The pH of the medium is preferably maintained at 3.0 to 9.0 during the culturing. The pH can be adjusted using inorganic or organic acid, an alkali solution, urea, calcium carbonate, ammonia or the like.

Also, antibiotics, such as ampicillin and tetracycline, can be added to the medium during culturing, if necessary.

When a microorganism transformed with an expression vector containing an inducible promoter is cultured, an inducer can be added to the medium, if necessary. For example, isopropyl-β-D-thidgalactopyranoside or the like can be added to the medium when a microorganism transformed with an expression vector containing lac promoter is cultured; or indoleacrylic acid or the like can be added thereto when a microorganism transformed with an expression vector containing trp promoter is cultured.

The medium for culturing a transformant obtained using an animal cell as the host includes generally used RPMI 1640 medium [*The Journal of the American Medical Association*, 199, 519 (1967)], Eagle's MEM medium [*Science*, 122, 501 (1952)], DMEM medium [*Virology*, 8, 396 (1959)], and 199 Medium [*Proceeding of the Society for the Biological Medicine*, 73, 1 (1950)], as well as media to which fetal calf serum or the like has been added to the above media and the like.

Culturing is generally carried out at pH 6 to 8 and at 25 to 40° C. for 1 to 7 days in the presence of 5% $CO_2$ or the like.

Furthermore, if necessary, antibiotics such as kanamycin, penicillin and streptomycin, can be added to the medium during the culturing.

The medium for culturing a transformant obtained using an insect cell as the host includes generally used TNM-FH medium (manufactured by Pharmingen), Sf-900 II SFM (manufactured by Life Technologies), ExCell 400 and ExCell 405 (both manufactured by JRH Biosciences), Grace's Insect Medium [*Nature*, 195, 788 (1962)] and the like.

Culturing is generally carried out at pH 6 to 7 and at 25to 30° C. for 1 to 5 days or the like.

Furthermore, if necessary, antibiotics such as gent amicin can be added to the medium during the culturing.

A transformant obtained by using a plant cell as the host cell can be used as the cell or after differentiating to a plant cell or organ. The medium used in the culturing of the transformant includes Murashige and Skoog (MS) medium, White medium, media to which a plant hormone, such as auxin or cytokinine, has been added, and the like.

Culturing is carried out generally at a pH 5 to 9 and at 20 to 40° C. for 3 to 60 days.

Also, antibiotics, such as kanamycin and hygromycin, can be added to the medium during the culturing, if necessary.

As described above, the protein having α1,4-galactosyltransferase activity can be produced by culturing a transformant derived from a microorganism, animal cell, insect cell or plant cell containing the recombinant DNA which comprises the DNA encoding the protein according to the general culturing method to produce and accumulate the protein, and recovering the protein from the culture.

In the production of the protein having α1,4-galactosyltransferase activity, the protein can be produced so as to have a structure as it is or can be produced as a secretory protein having a signal sequence or a fusion protein according to the method described in *Molecular Cloning*, Second Edition and the like The protein to be fused includes β-galactosidase, protein A, IgG binding region of protein A, chloramphenicol acetylransferase, poly(Arg), poly(Glu), protein G, maltose binding protein, glutathione S-transferase, polyhistidine chain (His-tag), S peptide, DNA binding protein domain, Tac antigen, thioredoxin, green fluorescent protein, FLAG peptide, epitope of any antibody, and the like [Akio Yamakawa, *Experimental Medicine* (*Jikken Igaku*), 13, 469–474 (1995)].

Furthermore, the process for producing the protein having α1,4-galactosyltransferase activity includes a process for production in which the protein is produced on an outer membrane of the host cell, and the process for production can be selected by changing the host cell used or the structure of the protein produced.

When the protein having α1,4-galactosyltransferase activity is produced in a host cell or on an outer membrane of the host cell, the produced protein can be actively secreted extracellularly according to, for example, the method of Paulson et al. [*J. Biol. Chem.*, 264, 17619 (1989)], the method of Lowe et al. [*Proc. Natl. Acad. Sci. USA*, 86, 8227 (1989); *Genes Develop.*, 4, 1288 (1990)], or the methods described in Japanese Published Unexamined Patent Application No. 336963/93, WO94/23021, and the like.

Specifically, the protein of the present invention can be actively secreted extracellularly by producing it in the form that a signal peptide has been added to the side of N-terminal of a protein containing an active site of the protein having α1,4-galactosyltransferase activity according to the recombinant DNA technique.

Furthermore, the protein production can be increased utilizing a gene amplification system using a dihydrofolate reductase gene or the like according to the method described in Japanese Published Unexamined Patent Application No. 227075/90.

Moreover, the protein having α1,4-galactosyltransferase activity can be produced by rediferentiating a gene-introduced animal or plant cell to develop a gene-introduced transgenic animal individual (transgenic nonhuman animal) or plant individual (transgenic plant), and using the individual.

When the transformant is the animal individual or plant individual, the protein can be produced by breeding or cultivating it to produce and accumulate the protein, and recovering the protein from the animal individual or plant individual.

The process for producing the protein having α1,4-galactosyltransferase activity using the animal individual includes a method for producing the protein of the present invention in a nonhuman animal developed by introducing a gene according to a known method [Am. J. Clin. Nutr., 63, 639S (1996), Am. J. Clin. Nutr., 63, 627S (1996), Bio/Technology, 9, 830 (1991)].

In the animal individual, the protein can be produced by breeding a transgenic nonhuman animal to which the DNA encoding the protein having α1,4-galactosyltransferase has been introduced to produce and accumulate the protein in the animal, and recovering the protein from the animal. The protein produced in the animal is accumulated in milk (Japanese Published Unexamined Patent Application No. 309192/88), egg, and the like. Any promoter can be used, so long as it can function in the animal. Suitable examples include an α-casein promoter, a β-casein promoter, a β-lactoglobulin promoter, a whey acidic protein promoter, and the like, which are specific for mammary glandular cells.

The process for producing the protein having α1,4-galactosyltransferase activity using the plant individual includes a process for producing the protein by cultivating a transgenic plant to which the DNA encoding the protein of the present invention is introduced by a known method [Tissue Culture (Soshiki Baiyo), 20 (1994), Tissue Culture (Soshiki Baiyo), 21 (1995), Trends Biotechnol., 15, 45 (1997)] to produce and accumulate the protein in the plant, and recovering the protein from the plant.

The protein produced by the production process of the protein of the present invention can be isolated and purified by using the general method for isolating and purifying an enzyme.

For example, when the protein having 1,4-galactosyltransferase activity is produced as a soluble product in the host cells, the cells are collected by centrifugation after culturing, suspended in an aqueous buffer, and disrupted using an ultrasonicator, a French press, a Manton Gaulin homogenizer, a Dynomill, or the like to obtain a cell-free extract.

From the supernatant obtained by centrifuging the cell-free extract, a purified product can be obtained by the general method used for isolating and purifying an enzyme, for example, solvent extraction, salting-out using ammonium sulfate or the like, desalting, precipitation using an organic solvent, anion exchange chromatography using a resin such as diethylaminoethyl (DEAE)-Sepharose or DIAION HPA-75 (manufactured by Mitsubishi Chemical), cation exchange chromatography using a resin such as S-Sepharose FF (manufactured by Pharmacia), hydrophobic chromatography using a resin such as butyl sepharose or phenyl sepharose, gel filtration using a molecular sieve, affinity chromatography, chromatofocusing, or electrophoresis such as isoelectronic focusing, alone or in combination thereof.

When the protein is produced as an inclusion body in the host cells, the cells are collected in the same manner, disrupted and centrifuged to recover the protein as the precipitate fraction, and then the inclusion body of the protein is solubilized with a protein-denaturing agent.

The solubilized solution is diluted or dialyzed in a solution free from a protein denaturing agent or a solution having a diluted concentration of a protein denaturing agent in such a degree that the protein is not denatured to thereby constitute the normal tertiary structure of the protein, and then a purified product of the protein can be obtained by a purification/isolation method similar to the above.

When the protein having α1,4-galactosyltransferase activity or derivatives such as its glycosylated-derivatives are secreted out of cells, the protein or its derivatives such as the glycosylated-derivatives can be collected in the culture supernatant.

Specifically, the culture medium is treated in a manner similar to the above, such as centrifugation to obtain a solubilized fraction, from which a purified product can be obtained using a purification/isolation method similar to the above.

The protein obtained by the above method includes a protein comprising the amino acid sequence represented by SEQ ID NO:1.

Furthermore, the protein having α1,4-galactosyltransferase activity is produced as a fusion protein with other protein, and can be purified using affinity chromatography using a substance having affinity to the fusion protein. For example, the fusion protein having α1,4-galactosyltransferase activity is produced as a fusion protein with protein A according to the method of Lowe et al. [Proc. Natl. Acad. Sci. USA, 86 8227 (1989); Genes Develop., 4, 1288 (1990)], or the method described in Japanese Published Unexamined Patent Application No. 336963/93 or WO94/23021, and the fusion protein can be purified by affinity chromatography using immunoglubulin G.

Moreover, the protein having α1,4-galactosyltransferase activity is produced as a fusion protein with Flag peptide, and the fusion protein can be purified by affinity chromatography using an anti-Flag antibody [Proc. Natl. Acad. Sci., USA, 86, 8227 (1989), Genes Develop., 4, 1288 (1990)]. In addition, purification can be carried out by affinity chromatography using the antibody against the polypeptide per se.

Based on the amino acid sequence information of the protein thus obtained, the protein having α1,4-galactosyltransferase can be produced by a chemical synthesis method, such as Fmoc (fluorenylmethyloxycarbonyl) method or tBoc (t-butyloxycarbonyl) method. It can also be chemically synthesized using a peptide synthesizer manufactured by Advanced ChemTech, Perkin-Elmer, Pharmacia, Protein Technology Instrument, Synthecell-Vega, PerSeptive, Shimadzu Corporation, or the like.

(3) Preparation of Galactose-Containing Complex Carbohydrate

A galactose-containing complex carbohydrate can be produced in an aqueous medium by allowing a culture of the transformant obtained by the culturing described in the above item [2] or a treated product of the culture as an enzyme source, uridine-5'-diphosphogalactose and an acceptor complex carbohydrate to be present in the aqueous medium to produce and accumulate the galactose-containing complex carbohydrate in the aqueous medium.

The treated product of the culture includes a concentrated product of the culture, a dried product of the culture, cells obtained by centrifuging the culture, a dried product of the cells, a freeze-dried product of the cells, a surfactant-treated product of the cells, an ultrasonic-treated product of the cells, a mechanically disrupted product of the cells, a solvent-treated product of the cells, an enzyme-treated product of the cells, a protein fraction of the cells, an immobilized product of the cells, an enzyme preparation obtained by extracting from the cell, and the like.

The acceptor complex carbohydrate used in the production of the galactose-containing complex carbohydrate is a complex carbohydrate comprising an oligosaccharide having galactose in its non-reducing terminal, preferably a complex carbohydrate comprising an oligosaccharide having a structure selected from the group consistnig of lactose, N-acetyllactosamine, lacto-N-tetraose, para-lacto-N-neohexaose and lacto-N-neotetraose in the non-reducing terminal, and more preferably a complex carbohydrate selected from the group consisting of lactose, N-acetyllactosamine, lacto-N-tetraose, para-lacto-N-neohexaose and lacto-N-neotetraose.

The enzyme source used in the production of the galactose-containing complex carbohydrate is used in a concentration of 1 mU/l to 1,000 U/l, preferably 10 mU/l to 500 U/l, when the activity capable of forming 1 µmol of galactose-containing complex carbohydrate at 37° C. in 1 minute is defined as 1 unit (U).

The aqueous medium used in the production of the galactose-containing complex carbohydrate includes water; a buffer such as a phosphate buffer, a carbonate buffer, an acetate buffer, a borate buffer, a citrate buffer and a tris buffer; alcohol, such as methanol and ethanol; ester such as ethyl acetate; ketone such as acetone; amide such as acetamide; and the like. Also, the culture of the microorganisms used as the enzyme source can be used as an aqueous medium.

In the production of the galactose-containing complex carbohydrate, a surfactant or an organic solvent may be added, if necessary. Any surfactant capable of accelerating the formation of a galactose-containing complex carbohydrate can be used as the surfactant. Examples include nonionic surfactants such as polyoxyethylene octadecylamine (e.g., Nymeen S-215, manufactured by Nippon Oil & Fats); cationic surfactants, such as cetyltrimethylammonium bromide and alkyldimethyl benzylammoniumchloride (e.g., Cation F2-40E, manufactured by Nippon Oil & Fats); anionic surfactants such as lauroyl sarcosinate; tertiary amines such as alkyldimethylamine (e.g., Tertiary Amine FB, manufactured by Nippon Oil & Fats); and the like, which are used alone or as a mixture of two or more. The surfactant is used generally in a concentration of 0.1 to 50 g/l. The organic solvent includes xylene, toluene, fatty acid alcohol, acetone, ethyl acetate, and the like, which are used in a concentration of generally 0.1 to 50 ml/l.

The production reaction for the galactose-containing complex carbohydrate is carried out in an aqueous medium having a pH 5 to 10, preferably pH 6 to 8, at 20 to 50° C. for 1 to 96 hours. In the production reaction, inorganic salts, such as $MnCl_2$ and $MgCl_2$, can be added, if necessary.

The amount of the galactose-containing complex carbohydrate produced in the aqueous medium can be determined, for example, using a carbohydrate analysis system manufactured by Dionex [*Anal. Biochem.*, 189:, 151 (1990)] or the like.

The galactose-containing complex carbohydrate produced in the aqueous medium can be recovered by the ordinary method using activated carbon, an ion exchange resin or the like.

Examples of the present invention are shown below; however, the present invention is not limited to these Examples.

Figure 1:
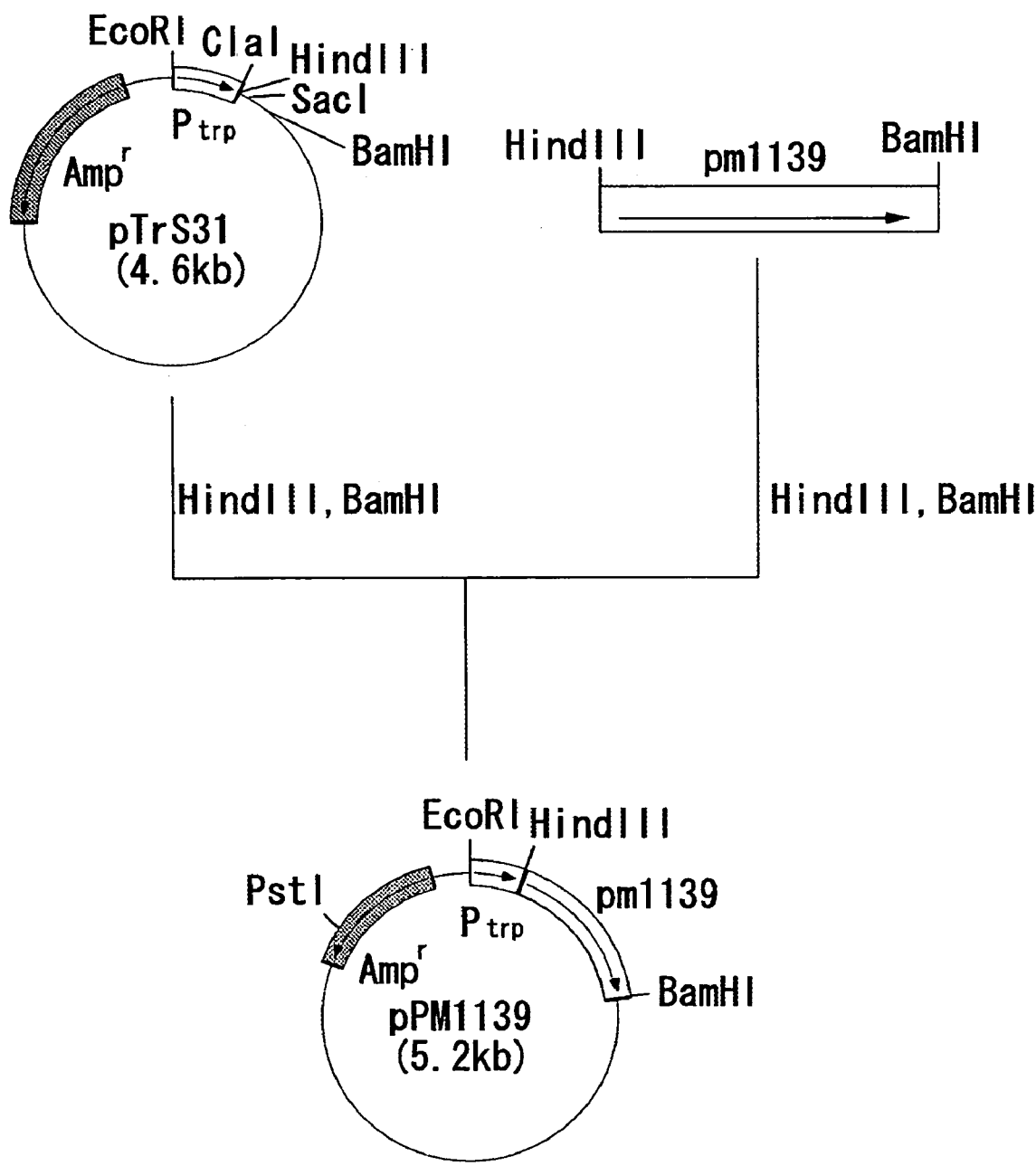
FIG. 1 shows construction steps of α1,4-galactosyltransferase gene expression plsmid pPM1139.

Also, in the drawing, Amp$^r$ represents an ampicillin-resistant gene; $P_{trp}$ represents tryptophane promoter; and pm1139 represents a gene encoding an α1,4-galactosyltransferase.

BEST MODE FOR CARRYING OUT THE INVENTION

EXAMPLE 1

Construction of a Strain Expressing a Gene Encoding α1,4-galactosyltransferase Derived from *Pasteurella multocida*

*Pasteurella multocida* PM70 was cultured by a known method [*FEMS Microbiol. Lett.*, 166 289 (1998)].

After the culturing, a chromosomal DNA of the microorganism was isolated and purified by the method described in *Current Protocols in Molecular Biology*.

Using DNA fragments having the nucleotide sequences represented by SEQ ID NOs:3 and 4 which had been synthesized by using a DNA synthesizer Model 8905 manufactured by Perceptive Biosystems, a DNA fragment containing pm1139 considered to be a gene encoding an α1,4-galactose transferase in the full nucleotide sequence of the genomic DNA in *Pasteurella multocida* PM70 was amplified by the following method.

PCR was carried out by using the above synthetic DNA fragments as a primer set and using the chromosomal DNA of *Pasteurella multocida* PM70 as the template. The PCR was carried out by using 40 µl of a reaction solution containing 0.1 µg of the chromosomal DNA, 0.5 µmol/l of each of the primers, 2.5 units of Pfu DNA polymerase (manufactured by Stratagene), 4 µl of 10×buffer solution for Pfu DNA polymerase and 200 µmol/l of each deoxy NTP, and repeating 30 times of a step consisting of 1 minute at 94° C., 2 minutes at 42° C. and 3 minutes at 72° C.

A ¹/₁₀ volume of the reaction solution was subjected to agarose gel electrophoresis to confirm that the fragment of interest was amplified, and then the remaining reaction solution was mixed with the same volume of TE [10 mmol/l Tris-HCl and 1 mmol/l EDTA (pH 8.0)] saturated phenol/chloroform (1 vol/1 vol).

After the mixed solution was centrifuged, the thus obtained upper layer was mixed with 2 volumes of cold ethanol and allowed to stand at −80° C. for 30 minutes. A precipitate of DNA was obtained by centrifuging the solution.

The DNA precipitate was dissolved in 20 μl of TE.

Using 5 μl of the dissolved solution, the DNA was digested with restriction enzymes HindIII and BamHI, the resulting DNA fragments were separated by agarose gel electrophoresis, and then a DNA fragment of 0.9 kb was recovered by using Gene Clean II Kit (purchased from Funakoshi).

After 0.2 μg of pBluescript II SK(+) was digested with restriction enzymes HindIII and BamHI, the resulting DNA fragments were separated by agarose gel electrophoresis, and then a DNA fragment of 2.9 kb was recovered in the same manner.

Using a ligation kit (manufactured by Takara Shuzo), the 0.9 kb and 2.9 kb fragments were subjected to ligation reaction at 16° C. for 16 hours. *Escherichia coli* NM522 was transformed by using the ligation reaction solution in accordance with the above known method, and the transformant was spread on an LB agar medium [10 g/l Bacto-Tryptone (manufactured by Difco), 10 g/l yeast extract (manufactured by Difco), 5 g/l sodium chloride and 15 g/l agarose] containing 50 μg/ml ampicillin, followed by culturing overnight at 30° C.

A plasmid was extracted from the thus formed transformant colonies in accordance with the above known method, the structure of the plasmid was confirmed by restriction enzyme digestion, and the plasmid was named pPM1139SK. The plasmid pPM1139SK has been deposited on Sep. 13, 2001, as FERM BP-7732 in International Patent Organism Depositary, National Institute of Advanced Industrial Science and Technology (postal code 305-8566; Central 6, 1-1-1 Higashi, Tsukuba, Ibaraki, Japan).

Next, pPM1139SK was digested with restriction enzymes HindIII and BamHI, the resulting DNA fragments were separated by agarose gel electrophoresis, and then a DNA fragment of 0.9 kb was recovered. After 0.2 μg of pTrS31 DNA was digested with restriction enzymes HindIII and BamHI, the resulting DNA fragments were separated by agarose gel electrophoresis, and then a DNA fragment of 4.3 kb was recovered in the same manner.

Using the ligation kit, the 0.9 kb and 4.3 kb fragments was subjected to ligation reactoin at 16° C. for 16 hours.

*Escherichia coli* NM522 was transformed by using the ligation reaction solution in accordance with the above known method, and the transformant was spread on the LB agar medium containing 50 μg/ml ampicillin, followed by culturing overnight at 30° C.

A plasmid was extracted from the thus formed transformant colonies in accordance with the above known method, thereby obtaining an expression plasmid pPM1139. The structure of the plasmid was verified by restriction enzyme digestion (FIG. 1).

EXAMPLE 2

Production of Galα1,4Galβ1,4Glc

*Escherichia coli* NM522/pPM1139 obtained in Example 1 was inoculated into a test tube charged with 8 ml of LB medium containing 50 μg/ml ampicillin, followed by culturing at 28° C. for 17 hours.

The culture was inoculated into a test tube charged with 8 ml of LB medium containing 50 μg/ml ampicillin, with an inoculum size of 1%, followed by culturing at 37° C. for 7 hours. Wet cells were obtained by centrifuging 0.1 ml of the culture. The wet cells can be stored at −20° C., if necessary, and it was able to use them by thawing prior to use.

The reaction was carried out at 37° C. for 10 hours in 0.1 ml of a reaction solution containing the NM522/pPM1139 wet cells (prepared from 0.1 ml of the culture), 50 mmol/l citrate buffer (pH 7.0), 10 mmol/l MnCl$_2$, 10 mmol/l lactose, 10 mmol/l UDP-galactose and 4 g/l Nymeen S-215.

After completion of the reaction, the reaction product was analyzed by using a sugar analyzer manufactured by Dionex (DX-500) under the following analyzing conditions to confirm that 7.6 mmol/l (3840 mg/l) of Galα1,4Galβ1,4Glc was formed and accumulated in the reaction solution.

| Analyzing conditions: | |
|---|---|
| Column: | CarboPAC PA10 |
| Eluent: | eluent A; H$_2$O, eluent B; 500 mmol/l NaOH |
| Gradient: | Linear gradient from a composition of 8% eluent B at 0 minute to a composition of 20% eluent B spending 21 minutes. |
| Detector: | Pulsed amperometry detector |

EXAMPLE 3

Examination on Substrate Specificity

*Escherichia coli* NM522/pPM1139 obtained in Example 1 was inoculated into a test tube charged with 8 ml of LB medium containing 50 μg/ml ampicillin, followed by culturing at 28° C. for 17 hours.

The culture was inoculated into a test tube charged with 8 ml of LB medium containing 50 μg/ml ampicillin, with an inoculum size of 1%, followed by culturing at 37° C. for 7 hours. Wet cells were obtained by centrifuging 0.1 ml of the culture. The wet cells can be stored at −20° C., if necessary, and it was able to use them by thawing prior to use.

Also, a strain NM522/pGT5 derived from *Neisseria gonorrhoeae* in which an α1,4-galactose transferase is expressed, which had been prepared in accordance with the method described in a reference [*Nat. Biotechnol.*, 16, 847 (1998)], was inoculated into a test tube charged with 8 ml of LB medium containing 50 μg/ml ampicillin, followed by culturing at 28° C. for 17 hours. The culture was inoculated into a test tube charged with 8 ml of LB medium containing 50 μg/ml ampicillin, with an inoculum size of 1%, followed by culturing at 30° C. for 4 hours and then at 40° C. for 3 hours, respectively. Wet cells were obtained by centrifuging 0.1 ml of the culture. The wet cells can be stored at −20° C., if necessary, and it was able to use them by thawing prior to use.

The reaction was carried out at 37° C. for 17 hours in 0.1 ml of a reaction solution containing 50 mmol/l citrate buffer (pH 7.0), 10 mmol/l MnCl$_2$, 10 mmol/l each receptor substrate, 10 mmol/l UDP-galactose and 4 g/l Nymeen S-215, using the NM522/pPM1139 wet cells or NM522/pPGT5 wet cells obtained in the above as enzyme sources. As the receptor substrates, N-acetyllactosamine (LacNAc: Galβ1,4GlcNAc), lacto-N-neotetraose (LNnT: Galβ1,4GlcNAcβ1,3Galβ1,4Glc), para-lacto-N-neohexaose (pLNnH: Galβ1,4GlcNAcβ1,3Galβ1,4GlcNAcβ1,3Galβ1,4Glc) and lacto-N-tetraose (LNT: Galβ1,3GlcNAcβ1,3Galβ1,4Glc) were used, in addition to lactose (Lac: Galβ1,4Glc). As a result, when the formed amount of globotriose (Galα1,4Galβ1,4Glc) produced by carrying out the reaction using NM522/pPGT5 wet cells as the enzyme source, and lactose as the substrate, was defined as 100, compounds in which galactose was respectively α1,4-bound to the non-reducing terminal of the substrate were produced at respective ratios shown in Table 1.

TABLE 1

| | Production ratio of galactose-containing complex carbohydrate | |
|---|---|---|
| Substrate | Strain pGT5 | Strain PM1139 |
| Lac | 100.0 | 129.6 |
| LacNAc | 8.5 | 100.5 |
| LNnT | 12.3 | 100.4 |
| pLNnH | 11.3 | 92.7 |
| LNT | 64.8 | 78.4 |

As a result, it was shown that a galactose-containing complex carbohydrate can be efficiently produced by using a protein having α1,4-galactosyltransferase activity derived from *Pasteurella multocida* in the case where LacNAc, LNnT or pLNnH is used as the substrate.

INDUSTRIAL APPLICABILITY

According to the present invention, an α1,4-galactosyltransferase can be produced in a large amount. Also, a galactose-containing complex carbohydrate can be produced efficiently by using the enzyme.

Free Text of Sequence Listing

SEQ ID NO:3—Description of artificial sequence: Synthetic DNA

SEQ ID NO:4—Description of artificial sequence: Synthetic DNA

The invention claimed is:

1. A process for producing a protein having α1,4-galactosyltransferase activity, which comprises: culturing a transformant capable of producing said protein in a medium to produce and accumulate the protein in the culture, and recovering said protein from said culture, wherein said protein comprises the amino acid sequence as set forth in SEQ ID NO:1.

2. The process according to claim 1, wherein the protein having α1,4-galactosyltransferase activity consists of the amino acid sequence as set forth in SEQ ID NO:1.

3. The process according to claims 1 or 2, wherein the transformant is transformed with a recombinant DNA encoding said protein.

4. The process according to claim 3, wherein the DNA encoding the protein having α1,4-galactosyltransferase activity comprises the nucleotide sequence as set forth in SEQ ID NO:2.

5. An isolated DNA comprising the nucleotide sequences as set forth in SEQ ID NO:2.

6. An isolated DNA consisting of the nucleotide sequence as set forth in SEQ ID NO:2.

* * * * *

UNITED STATES PATENT AND TRADEMARK OFFICE
CERTIFICATE OF CORRECTION

| | |
|---|---|
| PATENT NO. | : 7,232,674 B2 |
| APPLICATION NO. | : 10/490879 |
| DATED | : June 19, 2007 |
| INVENTOR(S) | : Tetsuo Endo et al. |

It is certified that error appears in the above-identified patent and that said Letters Patent is hereby corrected as shown below:

ON THE TITLE PAGE [56] REFERENCES CITED:

Foreign Patent Documents, "WO  WO  95/00595  1/2000" should read
--WO  WO  00/00595  1/2000--; and
Other Publications, "galactosytransferases" should read
--galactosyltransferases--.

ON THE TITLE PAGE [ABSTRACT]:

Line 2, "α1.4-galactosyltransferase" should read --α1,4-galactosyltransferase--; and
Line 4, "α1.4-galactosyltransferase" should read --α1,4-galactosyltransferase--

COLUMN 1:

Line 19, "*Chem.*, 275" should read --*Chem.*, 275,--.

COLUMN 4:

Line 3, "condition" should read --conditions--;
Line 9, "isms" should read --ism--; and
Line 45, "34" should read --34,-- and
    "*Research*, 13" should read --*Research*, 13,--.

COLUMN 5:

Line 31, "*USA*, 90,5873" should read --*USA*, 90, 5873--.

COLUMN 6:

Line 30, "*USA*, 98" should read --*USA*, 98,--.

COLUMN 7:

Line 2, "*USA*, 74" should read --*USA* 74,--, and
Line 4, "as 373A.DNA" should read --as 373A·DNA--.

UNITED STATES PATENT AND TRADEMARK OFFICE
CERTIFICATE OF CORRECTION

| | | |
|---|---|---|
| PATENT NO. | : 7,232,674 B2 | |
| APPLICATION NO. | : 10/490879 | |
| DATED | : June 19, 2007 | |
| INVENTOR(S) | : Tetsuo Endo et al. | |

It is certified that error appears in the above-identified patent and that said Letters Patent is hereby corrected as shown below:

COLUMN 8:

Line 36, "trp" should read --*trp*--;
    Line 37, "lac" should read --*lac*--;
    Line 41, "tac" should read --*tac*-- and
        "lacT7" should read --*lac*T7-- and
        "letI" should read --*let*I--; and
    Line 50, "lie" should read --lay--.

COLUMN 9:

Line 6, "*USA*, 69" should read --*USA*, 69,--;
    Line 9, "*Res.*, 16" should read --*Res.*, 16,--;
    Line 12, "YCp50(ATCC" should read --YCp50 (ATCC--; and
    Line 38, "*Biochem.*, 101" should read --*Biochem.*, 101,--.

COLUMN 11:

Line 33, "isopropyl-β-D-thidgalactopyranoside" should read
        --isopropyl-β-D-thiogalactopyranoside--; and
    Line 61, "25to" should read --25 to--.

COLUMN 12:

Line 57, "rediferentiating" should read --redifferentiating--.

COLUMN 14:

Line 21, "*USA*, 86" should read --*USA*, 86,--; and
    Line 25, "immunoglubulin" should read --immunoglobulin--.

COLUMN 15:

Line 49, "*Biochem.*, 189:," should read --*Biochem.*, 189,--.

UNITED STATES PATENT AND TRADEMARK OFFICE
CERTIFICATE OF CORRECTION

| | |
|---|---|
| PATENT NO. | : 7,232,674 B2 |
| APPLICATION NO. | : 10/490879 |
| DATED | : June 19, 2007 |
| INVENTOR(S) | : Tetsuo Endo et al. |

It is certified that error appears in the above-identified patent and that said Letters Patent is hereby corrected as shown below:

COLUMN 16:

Line 9, "*Lett.*, 166" should read --*Lett.*, 166,--;
    Line 43, "HindIII" should read --*Hind*III-- and
        "BamHI," should read --*Bam*HI;--; and
    Line 48, "HindIII" should read --*Hind*III--
        and "BamHI," should read --*Bam*HI;--.

COLUMN 17:

Line 4, "HindIII" should read --*Hind*III--
        and "BamHI," should read --*Bam*HI;--
    Line 7, "HindIII" should read --*Hind*III--;
    Line 8, "BamHI," should read --*Bam*HI,--;
    Line 11, "was" should read --were--;
    Line 12, "reactoin" should read --reaction--; and
    Line 36, "was able" should read --is possible--.

COLUMN 18:

Line 3, "was able" should read --is possible--; and
    Line 16, "was able" should read --is possible--.

UNITED STATES PATENT AND TRADEMARK OFFICE
CERTIFICATE OF CORRECTION

PATENT NO. : 7,232,674 B2
APPLICATION NO. : 10/490879
DATED : June 19, 2007
INVENTOR(S) : Tetsuo Endo et al.

It is certified that error appears in the above-identified patent and that said Letters Patent is hereby corrected as shown below:

COLUMN 24:

Line 22, "claims" should read --claim--; and
Line 29, "sequences" should read --sequence--.

Signed and Sealed this

Sixth Day of November, 2007

JON W. DUDAS
*Director of the United States Patent and Trademark Office*

UNITED STATES PATENT AND TRADEMARK OFFICE
CERTIFICATE OF CORRECTION

PATENT NO. : 7,232,674 B2
APPLICATION NO. : 10/490879
DATED : June 19, 2007
INVENTOR(S) : Tetsuo Endo et al.

It is certified that error appears in the above-identified patent and that said Letters Patent is hereby corrected as shown below:

ON THE TITLE PAGE 1361 REFERENCES CITED:

Foreign Patent Documents, "WO  WO  95/00595  1/2000" should read
--WO  WO  00/00595  1/2000--; and
Other Publications, "galactosytransferases" should read
--galactosyltransferases--.

ON THE TITLE PAGE [ABSTRACT]:

Line 2, "α1.4-galactosyltransferase" should read --α1,4-galactosyltransferase--; and
Line 4, "α1.4-galactosyltransferase" should read --α1,4-galactosyltransferase--

COLUMN 1:

Line 19, "*Chem.*, 275" should read --*Chem.*, 275,--.

COLUMN 4:

Line 3, "condition" should read --conditions--;
Line 9, "isms" should read --ism--; and
Line 45, "34" should read --34,-- and
"*Research*, 13" should read --*Research*, 13,--.

COLUMN 5:

Line 31, "*USA*, 90,5873" should read --*USA*, 90, 5873--.

COLUMN 6:

Line 30, "*USA*, 98" should read --*USA*, 98,--.

COLUMN 7:

Line 2, "*USA*, 74" should read --*USA* 74,--, and
Line 4, "as 373A.DNA" should read --as 373A•DNA--.

UNITED STATES PATENT AND TRADEMARK OFFICE
CERTIFICATE OF CORRECTION

PATENT NO. : 7,232,674 B2
APPLICATION NO. : 10/490879
DATED : June 19, 2007
INVENTOR(S) : Tetsuo Endo et al.

It is certified that error appears in the above-identified patent and that said Letters Patent is hereby corrected as shown below:

COLUMN 8:

Line 36, "trp" should read --*trp*--;
       Line 37, "lac" should read --*lac*--;
       Line 41, "tac" should read --*tac*-- and
            "lacT7" should read --*lac*T7-- and
            "letI" should read --*let*I--; and
       Line 50, "lie" should read --lay--.

COLUMN 9:

Line 6, "*USA*, 69" should read --*USA*, 69,--;
       Line 9, "*Res.*, 16" should read --*Res.*, 16,--;
       Line 12, "YCp50(ATCC" should read --YCp50 (ATCC--; and
       Line 38, "*Biochem.*, 101" should read --*Biochem.*, 101,--.

COLUMN 11:

Line 33, "isopropyl-β-D-thidgalactopyranoside" should read
            --isopropyl-β-D-thiogalactopyranoside--; and
       Line 61, "25to" should read --25 to--.

COLUMN 12:

Line 57, "rediferentiating" should read --redifferentiating--.

COLUMN 14:

Line 21, "*USA*, 86" should read --*USA*, 86,--; and
       Line 25, "immunoglubulin" should read --immunoglobulin--.

COLUMN 15:

Line 49, "*Biochem.*, 189:," should read --*Biochem.*, 189,--.

COLUMN 16:

Line 9, "*Lett.*, 166" should read --*Lett.*, 166,--;
       Line 43, "HindIII" should read --*Hind*III-- and
            "BamHI," should read --*Bam*HI;--; and
       Line 48, "HindIII" should read --*Hind*III-- and
            "BamHI," should read --*Bam*HI;--.

UNITED STATES PATENT AND TRADEMARK OFFICE
CERTIFICATE OF CORRECTION

PATENT NO. : 7,232,674 B2
APPLICATION NO. : 10/490879
DATED : June 19, 2007
INVENTOR(S) : Tetsuo Endo et al.

Page 3 of 3

It is certified that error appears in the above-identified patent and that said Letters Patent is hereby corrected as shown below:

<u>COLUMN 17</u>:

Line 4, "HindIII" should read --*Hind*III-- and
        "BamHI," should read --*Bam*HI;--
    Line 7, "HindIII" should read --*Hind*III--;
    Line 8, "BamHI," should read --*Bam*HI,--;
    Line 11, "was" should read --were--;
    Line 12, "reactoin" should read --reaction--; and
    Line 36, "was able" should read --is possible--.

<u>COLUMN 18</u>:

Line 3, "was able" should read --is possible--; and
    Line 16, "was able" should read --is possible--.

<u>COLUMN 24</u>:

Line 22, "claims" should read --claim--; and
    Line 29, "sequences" should read --sequence--.

This certificate supersedes Certificate of Correction issued November 6, 2007.

Signed and Sealed this

Fourth Day of December, 2007

JON W. DUDAS
*Director of the United States Patent and Trademark Office*